(12) United States Patent
Stockert

(10) Patent No.: US 8,361,064 B2
(45) Date of Patent: Jan. 29, 2013

(54) DEVICE FOR THERMOSURGERY

(76) Inventor: Rüdiger Stockert, Freiburg (DE)

( * ) Notice: Subject to any disclaimer, the term of this patent is extended or adjusted under 35 U.S.C. 154(b) by 539 days.

(21) Appl. No.: 12/668,897

(22) PCT Filed: Jul. 16, 2007

(86) PCT No.: PCT/EP2007/006302
§ 371 (c)(1),
(2), (4) Date: Feb. 18, 2010

(87) PCT Pub. No.: WO2009/010080
PCT Pub. Date: Jan. 22, 2009

(65) Prior Publication Data
US 2010/0211062 A1     Aug. 19, 2010

(51) Int. Cl.
*A61B 18/12* (2006.01)
(52) U.S. Cl. .......................................... 606/34
(58) Field of Classification Search ............... 606/33, 606/34, 41
See application file for complete search history.

(56) References Cited

U.S. PATENT DOCUMENTS

| 6,962,587 B2 | 11/2005 | Johnson et al. |
| 2004/0078038 A1 | 4/2004 | Desinger et al. |
| 2005/0113819 A1 | 5/2005 | Wham et al. |

FOREIGN PATENT DOCUMENTS

| DE | 2353013 | 5/1974 |
| DE | 3120102 C2 | 12/1982 |
| DE | 4126607 A1 | 2/1993 |
| EP | PCT/ISA/210 | 10/2007 |

*Primary Examiner* — Michael Peffley
*Assistant Examiner* — Daniel Fowler
(74) *Attorney, Agent, or Firm* — Mesmer & Deleault, PLLC

(57) ABSTRACT

An apparatus for the thermosurgical treatment of biological tissue comprises a generator (22) for providing treatment energy, measuring means (24) for registering the temporal progression of a measured quantity that is influenced by the tissue impedance of the treated body or representative of the tissue impedance, and also a control unit (26) which has been set up to ascertain a frequency spectrum within a predetermined examination frequency range for the temporal progression of the measured quantity and to control the energy output of the generator (22) in a manner depending on the spectral content of the measured quantity within the examination frequency range. The invention is based on the finding that the genesis of vapor bubbles in the heated tissue can be detected on the basis of the frequency spectrum of the tissue impedance, in particular within a frequency range between approximately 0.5 kHz and 200 Hz. Depending on the extent of the vapor bubbling, the tissue impedance displays a differing spectral image within this frequency range. In accordance with the invention, this finding is utilized for the purpose of controlling the energy output of the generator.

21 Claims, 3 Drawing Sheets

DEVICE FOR THERMOSURGERY

Figure 1:
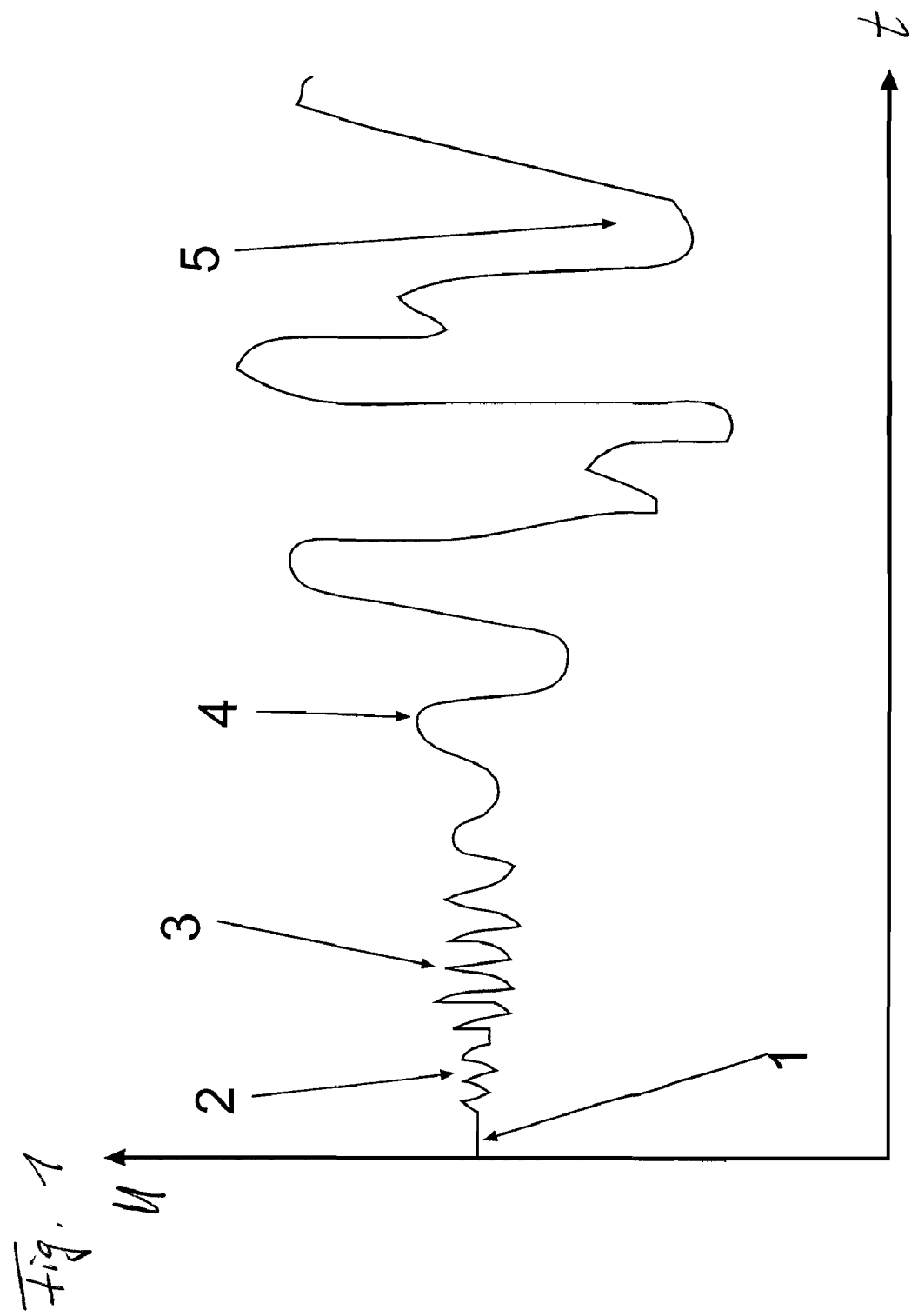

The invention relates to an apparatus for thermal surgery.

In thermal surgery biological tissue is heated by introduction of treatment energy, in order to achieve a defined therapeutic aim by denaturation of the treated tissue. In particular, in thermal surgery a coagulation or ablation of local tissue regions is striven for, for example on the inner cardiac wall of the heart chambers, on the valves of the heart chambers, on the veins and arteries connected to the heart, or on other blood-conveying vessels of the human or animal body. In respect of the heart, cases of arrhythmia or tachycardia, for example, can be treated by means of thermal surgery. It will be understood that the field of application of the thermosurgical apparatus according to the invention is not restricted to cardiac treatments. In principle, the apparatus according to the invention is suitable for the thermosurgical treatment of arbitrary sites on or within the body.

Various methods are known for the introduction of the treatment energy, including application of a high-frequency a.c. voltage, oscillating as a rule within the two-digit or three-digit kHz range, via electrodes attached to the body (one then speaks of HF surgery), or irradiation with ultrasound, laser light or microwaves. Again, in principle the apparatus according to the invention is not subject to any restriction as regards the type of the generation of heat in the treated tissue, be it electrical or by means of other active mechanisms.

In the course of thermal treatment of biological tissue with the aim of the denaturation thereof it is known that the impedance of the tissue changes with the tissue temperature. In particular, it is known that the tissue impedance firstly decreases with increasing heating, before the lowering of the impedance is attenuated and the curve of the impedance characteristic becomes flat, but that the tissue impedance then often shoots up jerkily. In order to avoid undesirable charring or scabbing of the tissue, frequently the aim is to control the input of energy into the tissue in such a way that the tissue impedance remains within the region of its declining or flattened characteristic branch but in no case is the strongly ascending branch of the impedance characteristic attained. For this purpose it is known to measure the tissue impedance continuously and, on the basis of the measured impedance, to control manually or automatically the energy output of a generator providing the treatment energy. In DE 31 20 102 C2, for example, the derivative of the temporal progression of the tissue impedance is ascertained, and the power of the generator is reduced if the derivative attains a value close to zero. It has certainly been shown that for many applications even this method is not sufficiently reliable for controlling the power of the generator.

It is therefore the object of the invention to create an apparatus for thermal surgery that is able to avoid undesirable charring or scabbing of the treated tissue reliably.

With a view to achieving this object, an apparatus according to the invention for thermal surgery includes a generator for providing treatment energy, measuring means for registering the temporal progression of a measured quantity that is influenced by the tissue impedance of the treated body or that is representative of the tissue impedance, and also a control unit which has been set up to ascertain a frequency spectrum within a predetermined examination frequency range for the temporal progression of the measured quantity and to control the energy output of the generator in a manner depending on the spectral content of the measured quantity within the examination frequency range.

The finding underlying the invention is that in biological tissue, when it is heated, microscopically small bubbles arise which find expression in the tissue impedance by virtue of a characteristic spectrum varying in temperature-dependent manner. By ascertainment and evaluation of the frequency spectrum of the tissue impedance, in this way the current temperature in the treated tissue can be inferred, and, depending thereon, the power of the generator can be controlled. Since, prior to a charring or scabbing of the tissue, bubbling can firstly always be detected within the tissue or on the surfaces of applied electrodes (human or animal tissue consists, to a not insignificant extent, of an aqueous saliferous solution, the water contained therein evaporating upon heating and turning into vapour bubbles), by suitable control of the power of the generator upon appearance of the bubbles undesirably severe damage to the tissue can be safely avoided. Via the frequency spectrum of the tissue impedance or, expressed generally, of a measured quantity influenced by the tissue impedance or representing the latter, the bubbling and the intensity thereof can be reliably detected.

It has been shown that the bubbles arising upon heating of the tissue disappear more or less quickly. Within a few fractions of a second they may cool again so considerably on account of the cooling effect by virtue of the colder environment that they dissolve. It has furthermore been shown that with increasing input of energy into the tissue and with increasing heating of the tissue the size of the is vapour bubbles and their lifespan (residence-time) increase, but simultaneously the number of bubbles arising per unit of time (frequency) decreases.

In particular, the following relationship was observed: at comparatively low temperature many small bubbles with comparatively short lifespan arise; at medium temperature moderately many bubbles with medium size and medium lifespan arise; at comparatively high temperatures, on the other hand, comparatively few bubbles with large size and long lifespan arise. As a rule of thumb, the following was accordingly established: the bubble size and the lifespan are proportional to the temperature, whereas the frequency of occurrence of the bubbles is inversely proportional to the temperature. It was further observed that the temperature of the onset of bubbling lies, as a rule, above 40° C.

A direct optical or other registration of these fine bubbles is not possible, or only possible with difficulty, with present-day medical instruments. It has to be considered that many interventions take place without a view of the site of the operation, for example in the closed heart chamber or in deep regions of the brain.

The invention takes advantage of the fact that the vapour bubbles influence the tissue impedance. In concrete terms, they become noticeable through fluctuations in tissue impedance. These fluctuations can be registered via a spectral analysis of a measured quantity depending on the tissue impedance. It has been shown in experiments that the changes in tissue impedance caused by bubbles typically exhibit frequencies between 80 Hz down to below 1 Hz. The higher frequencies were observed at temperatures around 40° C. to 50° C. Since many small bubbles with short lifespan arise at these comparatively low temperatures, the resulting fluctuations in impedance have comparatively small amplitude but arise at comparatively high speed. The low frequencies down to below 1 Hz, on the other hand, were predominantly observed at comparatively high temperatures between 80° C. and 100° C. At these temperatures, large bubbles with long lifespan predominate, which bring about slow but comparatively strong changes in tissue impedance. In particular, it was established that the fluctuations in tissue impedance at the high temperatures may be greater than at the low temperatures by a two-digit or even three-digit factor, for example 200 times to 500 times as great.

The control unit of the thermosurgical apparatus according to the invention utilises the above finding of a relationship between the tissue temperature and the spectrum of the tissue impedance by controlling the energy output of the generator in a manner depending on the spectral content of the analysed measured quantity within a predetermined examination frequency range. The upper limit of the examination frequency range preferentially lies at most at approximately 5 kHz and at least at approximately 80 Hz, preferentially at least at approximately 100 Hz, and most preferentially at least at approximately 200 Hz. The lower limit of the examination frequency range, on the other hand, preferentially lies at most at approximately 2 Hz and at least at approximately 1 Hz, preferentially at least at approximately 0.5 Hz, and most preferentially at least at approximately 0.1 Hz.

Within the examination frequency range evaluated by the control unit it cannot be ruled out that, besides the spectral components caused by bubbles, other components arise that are to be attributed to other causes. In particular, components that are caused by the cardiac activity may be superimposed on the spectral components caused by bubbles. However, such spectral components caused by the heartbeat arise only periodically. By time-periodic filtering (blanking) of the signal of the measured quantity, the spectral components caused by the heartbeat can be removed from the frequency spectrum of the measured quantity.

Depending on the technology that is employed (e.g. calculation by means of discrete Fourier analysis, analogue filter banks or such like), the frequency spectrum can be re-ascertained by the control unit in continuous-time manner or at regular, sufficiently short time-intervals. The current frequency spectrum in each instance is then evaluated by the control unit and—if necessary—converted into corresponding control commands for the generator, in order to raise or lower its output energy. For the evaluation of the frequency spectrum, the control unit may have been set up to ascertain from the frequency spectrum at least one characteristic spectral parameter of the frequency spectrum of the measured quantity, for instance a characteristic frequency or a characteristic amplitude. For example, a characteristic frequency may be that frequency at which the frequency spectrum within the examination frequency range has a (local or global) amplitude maximum. A characteristic amplitude may be, for example, the amplitude at such a (local or global) amplitude maximum of the spectrum.

From the above elucidations relating to the temperature dependence of the bubbling process it can be seen that a characteristic frequency defined in such a way will shift towards smaller frequency values in the case of rising tissue temperature, whereas simultaneously the maximum amplitude of the frequency spectrum will become increasingly larger. Therefore the control unit may expediently have been set up to lower the power of the generator during a treatment procedure in response to a diminution of the value of the characteristic frequency or/and in response to an increase in the value of the characteristic amplitude.

It will be understood that other definitions of a characteristic frequency and a characteristic amplitude, or generally of the at least one characteristic spectral parameter, are possible. For example, a characteristic frequency could be defined as the centre frequency of a defined frequency range of the ascertained frequency spectrum, for instance of a frequency range within which the frequency spectrum lies above a predetermined amplitude threshold. A characteristic amplitude could be defined, for example, as an amplitude average that is obtained by weighted or unweighted averaging of the spectral amplitude within a defined frequency range of the ascertained frequency spectrum.

It is also conceivable to ascertain several differently defined characteristic frequencies or/and several differently defined characteristic amplitudes from the frequency spectrum of the measured quantity and to undertake the control of the energy output of the generator on the basis of each of the characteristic frequencies or each of the characteristic amplitudes. Expediently the at least one characteristic spectral parameter should be defined in such a way that it (or they, if several characteristic spectral parameters are defined) displays a pattern that is variable in temperature-dependent manner and that is a measure of the tissue temperature.

In one embodiment of the invention, the control unit has been set up to derive, in a manner depending on a plurality of input parameters, at least some of which are characteristic of the ascertained frequency spectrum, an auxiliary parameter that is representative of the tissue temperature, and to control the energy output of the generator in a manner depending on the value of the auxiliary parameter. In this connection the control unit for the derivation of the auxiliary parameter may expediently access stored information via a relationship, ascertained in advance, between the input parameters and the tissue temperature. This relationship may, for example, be obtained in advance by empirical methods through experiment. The stored information may express the relationship functionally in the form of an algorithm, for example. It may also express it in the form of a table or a set of tables. In a preferred embodiment, the input parameters include both a characteristic frequency and a characteristic amplitude of the ascertained frequency spectrum.

For the energy output of the generator, a regulation that is continuous at least in time segments is conceivable, in the course of which the control unit adjusts the energy output of the generator to a predetermined or predeterminable desired value or to a desired-value profile of the auxiliary parameter.

Alternatively or additionally, it is conceivable that the control unit has been set up to change the energy output of the generator in a manner depending on the crossing of at least one predetermined threshold of the auxiliary parameter, in particular in stepped manner. For example, it may be the case that the control unit switches the generator off at least temporarily if a limit temperature of the tissue indicated by a corresponding threshold is exceeded.

It has been shown that the frequency spectrum of the measured quantity may depend on further influencing factors in addition to the tissue temperature. The input parameters from which the control unit ascertains the auxiliary parameter may therefore include, besides the at least one characteristic spectral parameter of the ascertained frequency spectrum, additionally one or more further parameters that are representative of the further influencing factors mentioned above and that are not derived from the ascertained spectrum. One of the influencing factors may be, in particular, the air pressure.

It has been shown that the prevailing air pressure may have a considerable influence on the bubbling and hence on the impedance spectrum. It is known that the partial pressure of the vapour bubbles in the biological tissue (e.g. heart chamber or blood vessels) changes with the external pressure (air pressure). A high external pressure shifts the temperature threshold, starting from which the bubbling sets in, upwards. A lower external pressure, on the other hand, permits vapour bubbling already at significantly lower temperatures. With a view to more precise determination of the tissue temperature and, as a result, of the size and depth of the heated tissue region, it has therefore proved expedient to take account of the air pressure in connection with the control of the energy output of the generator. For example, for this purpose the control unit may receive from a pressure sensor a sensor signal that is representative of the measured air pressure. It is also conceivable that the user can set an air-pressure value on the apparatus manually and that the control unit draws upon the air-pressure value predetermined by the user.

The consideration of those input parameters which the control unit does not derive from the ascertained frequency spectrum but receives in some other way (by sensory measurement, user default) in connection with the control of the generator may, for example, be effected in such a manner that the control unit ascertains from the at least one spectrum-related input parameter firstly a preliminary value of the auxiliary parameter and then corrects this preliminary value multiplicatively or additively by means of one or more correction factors, in order in this way to arrive at a definitive value of the auxiliary parameter. The control unit can take the value of the respective correction factor from, for example, a correction table ascertained and stored in advance. Such a correction table is to be understood as part of the aforementioned information concerning the relationship between the input parameters and the tissue temperature.

Correction factors may, for example, also have been provided for influencing factors such as the type of tissue or such as the location and/or type of an electrode via which an electrical signal that is drawn upon for the ascertainment of the measured quantity is tapped on the body. For instance, it has been shown that the vapour bubbles may behave differently in tissue that is intensely supplied with blood than in comparatively hard tissue layers. Furthermore, it has been shown that different measured values may result at skin electrodes or surface electrodes than at passive measuring electrodes for electrophysiological signals or at active high-frequency electrodes with which an electrical a.c. voltage is applied to the tissue in the course of the HF surgery.

According to an advantageous further development of the invention, the control unit may have been set up to present the ascertained frequency spectrum or at least one quantity derived therefrom on a display unit for visual representation. This permits the operating surgeon a personal examination of the course of the treatment and, where appropriate, an adaptation of the output power of the generator via suitable operating elements on the apparatus according to the invention.

Figure 2:
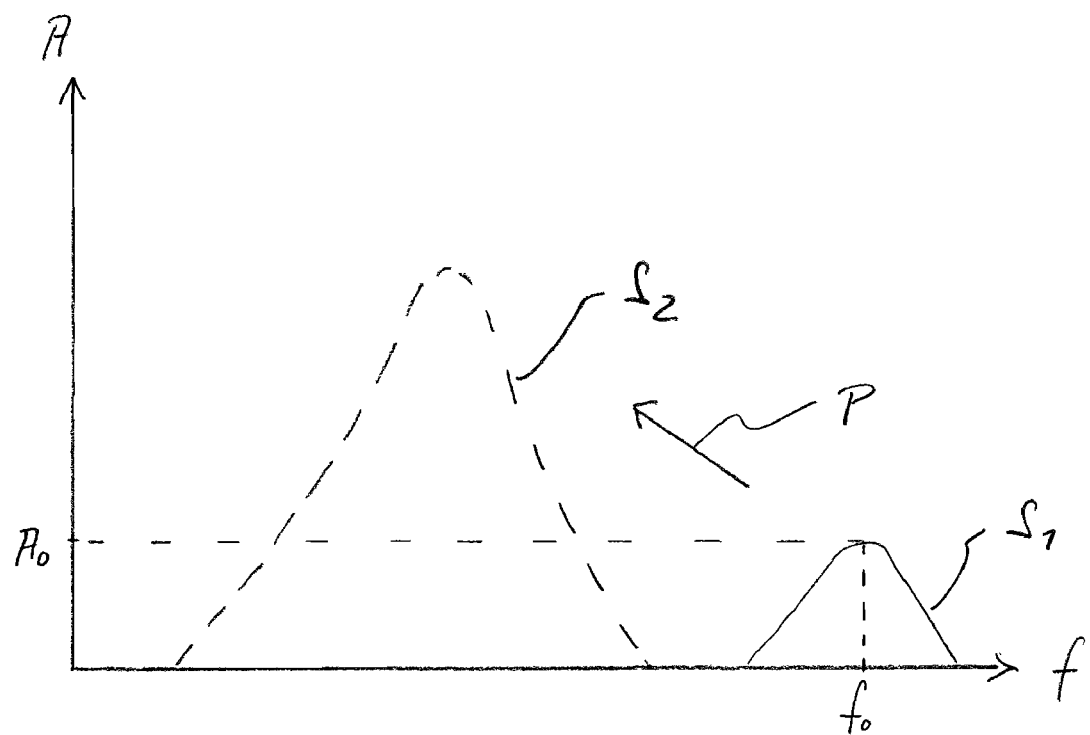
Figure 3:
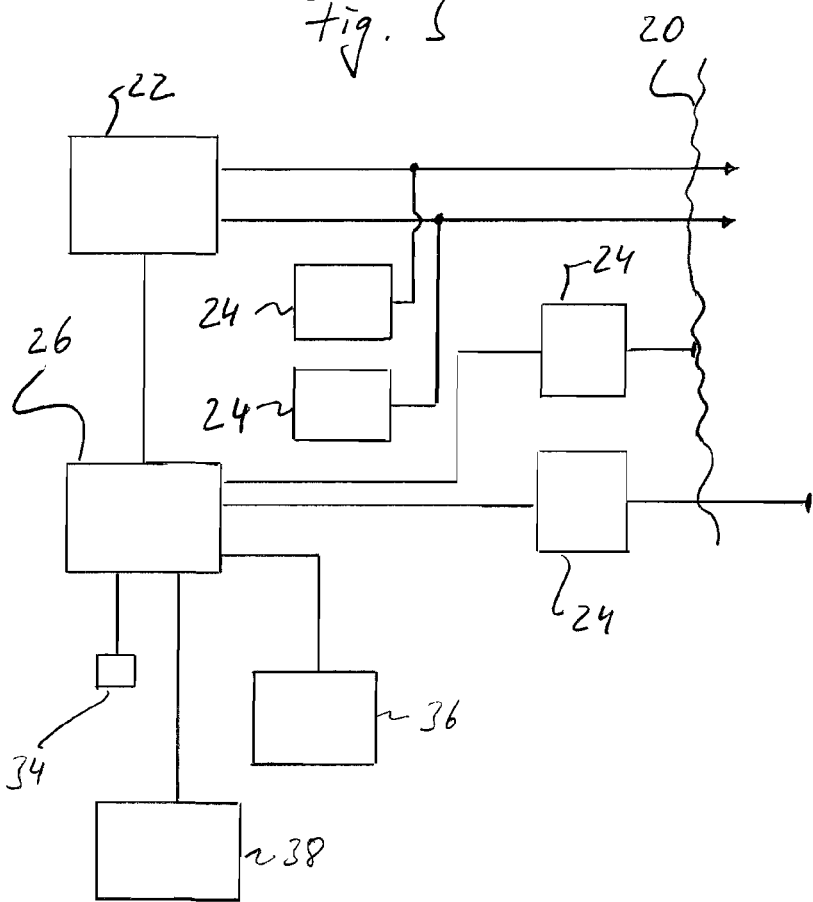
Figure 4:
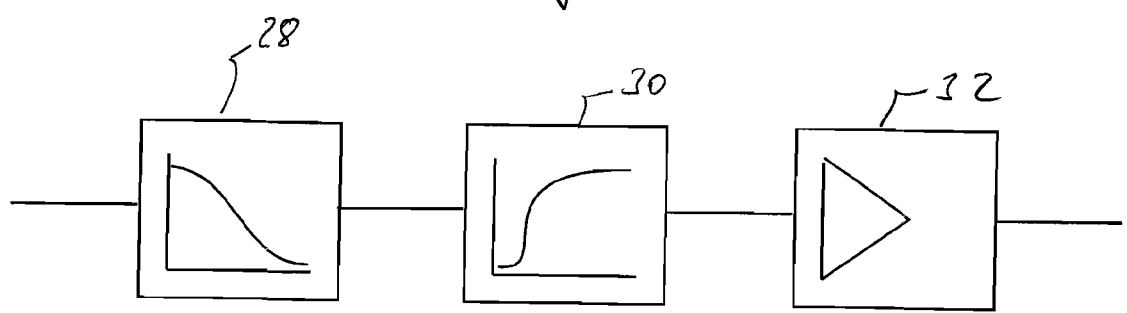

The invention will be elucidated further in the following on the basis of the appended drawings. Represented are:

FIG. 1: an exemplary temporal progression, to be understood purely qualitatively, of a voltage-measuring signal in which fluctuations become evident which are to be attributed to the formation of vapour bubbles in the tissue during a thermosurgical application, FIG. 2: schematically and again purely qualitatively, the changing frequency spectrum of the tissue impedance in the case of increasing heating of the tissue, FIG. 3: schematically, a block diagram of an exemplary embodiment of a thermosurgical apparatus according to the invention and FIG. 4: components of a measuring amplifier of the apparatus shown in FIG. 3.

FIG. 1 shows a typical electrophysiological voltage signal such as can be tapped on a living body. For example, the voltage signal may be tapped at the application part of a cardiac catheter, at internal lead electrodes of such a cardiac catheter, at ECG electrodes or reference electrodes attached to the body externally or at a counter-electrode. The diagram shown in FIG. 1 clarifies the fluctuations of the voltage amplitude which are observable in the course of the thermosurgical treatment of the body, caused by vapour bubbling in the tissue and, associated therewith, by a change in tissue impedance. It is to be stressed once again that the representation in FIG. 1 is to be understood purely qualitatively; in particular, no inferences of the actual ratios are to be deduced from the represented ratio of the intensity of the voltage fluctuations caused by bubbles to the base level of the voltage signal. In practice, the voltage fluctuations caused by bubbles may be small in comparison with the base level of the voltage-measuring signal.

Identified by arrows in the diagram shown in FIG. 1 are a total of five different phases, which are associated with differing degrees of heating of the tissue and hence with differing degrees of vapour bubbling. Phase 1 labels the start of the input of energy into the tissue; as yet, no excursions in the voltage-measuring signal can be discerned. However, vapour bubbling sets in already upon slight heating of the tissue. It becomes noticeable in the voltage-measuring signal through comparatively weak voltage fluctuations. The fluctuations arise relative quickly, i.e. they have a relatively high frequency. This is phase 2 in the diagram shown in FIG. 1.

Upon further increase of the temperature of the tissue the voltage fluctuations become steadily greater. At the same time, the speed of these artefacts decreases. In the frequency spectrum this becomes noticeable through correspondingly lower frequencies with simultaneously higher spectral amplitude. Phases 3 and 4 in the diagram shown in FIG. 1 clarify this increase in the intensity of fluctuation with simultaneously decreasing frequency of the changes in voltage.

Upon intense heating of the tissue, the voltage fluctuations arising are greater still. The amplitude of these voltage fluctuations reaches its maximum. At the same time, the frequency of the voltage fluctuations falls greatly.

FIG. 2 clarifies, again purely qualitatively, the associated spectrum of the voltage signal within the frequency range that is relevant to vapour bubbling. This frequency range ranges, for example, from 0.5 Hz to approximately 200 Hz, although the upper and lower limits of the frequency range investigated may, of course, be chosen differently in the concrete application. The spectrum of the changes in tissue impedance brought about by vapour bubbling, and hence in the voltage fluctuations of the measuring signal upon slight heating of the tissue, is denoted in FIG. 2 by $S_1$, whereas the spectrum upon intense heating is denoted by $S_2$ and, in contrast to the spectrum upon slight heating, is only indicated by dashes.

The spectral envelopes sketched in FIG. 2 are, of course, to be understood as being exemplary only; in the concrete application the spectra may display a different shape. What is important is merely the fact that with increasing heating a shift of the spectrum towards lower frequencies takes place, while the spectral amplitude simultaneously becomes larger. This behaviour is represented in FIG. 2 by a shift arrow P pointing towards lower frequencies and towards larger spectral amplitudes.

The temperature-dependent shift of the tissue-impedance spectrum is exploited in accordance with the invention in order to control the input of energy into the tissue. In particular, the power of the generator can be cut back before the spectrum drifts too far towards low frequencies, in order in this way to avoid burns and scabbing of the tissue.

It has been shown that for the identification of the spectral content of the tissue-impedance spectrum two defined spectral parameters are particularly suitable, namely the frequency of greatest amplitude (labelled in FIG. 2 by $f_0$) and also the maximum spectral amplitude (labelled by $A_0$). From the above elucidations it can readily be seen that these two parameters change with increasing heating of the tissue: whereas the value of the frequency $f_0$ decreases, the value of the amplitude $A_0$ becomes greater. With given boundary conditions, the value pair $(f_0/A_0)$ is a reliable indicator of the current tissue temperature. The corresponding relationship between these spectral parameters and the tissue temperature can be ascertained experimentally, for example, and recorded in characteristic form or in the form of a functional expression. It should be pointed out that it is generally not excluded to use solely the spectral parameter $f_0$ or solely the spectral parameter $A_0$ (where appropriate in conjunction with further influencing parameters that are independent of the spectrum of the tissue impedance) in connection with the control of the input of energy into the tissue. For each of the named spectral parameters alone also displays a characteristic behaviour that is dependent on the tissue temperature.

In the block diagram illustrated in FIG. 3 a biological tissue 20 is indicated, into which a coagulation instrument or ablation instrument, not represented in any detail, is introduced. Via the instrument and an electrode arrangement provided on the instrument, an electrical a.c. voltage is applied to the tissue 20 by a high-frequency generator 22. Typically the frequency of the a.c. voltage employed for the tissue treatment lies within the three-digit kHz range right up to the one-digit MHz range. For example, it amounts to approximately 200 kHz or approximately 500 kHz. In the case of bipolar instruments the treatment alternating voltage is applied between two electrodes attached to the tip of the instrument that has been introduced; in the case of monopolar instruments only the application electrode is located at the tip of the instrument; the counter-electrode is located externally on the surface of the treated body. The invention is generally independent of the type of instrument used and also independent of the type of the introduced treatment energy, be it electrical energy, electromagnetic energy, optical energy or acoustic energy.

For the purpose of registering the vapour bubbling, which arises as a consequence of the increasing heating of the treated tissue, use is made of transducers 24 which in each instance tap an electrical measurement voltage via an electrode attached to the body internally or externally, subject said measurement voltage to band-pass filtering and amplify it and supply the measured signal obtained in this way to an electronic control unit 26. In the exemplary case of FIG. 2 a total of four transducers 24 are shown. In each case a transducer 24 is preferentially connected at least to each of the active HF electrodes via which the treatment alternating voltage of the generator 22 is fed into the tissue 20 (application electrode as well as indifferent or neutral electrode); these transducers are, as a rule, the primary locations of the evolution of heat. The number of transducers 24 is, of course, variable at any time. It may be sufficient to tap only a single measurement voltage on the body. In many applications, however, it will be expedient to tap measurement voltages at various places on the body (internally or/and externally), in order in this way to be able to detect instances of possible local overheating of the tissue in different regions of the body. In this connection it should be pointed out that external electrodes that have not been attached properly may result in locally increased current densities and, in the worst case, undesirable burns. Such instances of undesirable overheating of the tissue can also be prevented with the thermosurgical apparatus according to the invention, by the power of the generator being already brought down upon the occurrence of slight bubbling.

According to FIG. 4, each of the transducers 24 exhibits by way of functional components a low-pass filter 28, a high-pass filter 30 and also a subsequent amplification module 32. The two filters 28, 30 together bring about a band-pass filtering of the measured signal, the pass band being, for example, between approximately 0.5 Hz and approximately 200 Hz. Within this range the relevant portion of the spectral components associated with the formation of vapour arises, according to the prior state of knowledge.

The control unit 26 then ascertains a frequency spectrum for each of the band-pass-filtered and amplified measured signals, for example by Fourier analysis or other suitable spectral examination methods. For each frequency spectrum ascertained in this way it ascertains the current values of the spectral parameters $f_0$ and $A_0$ and ascertains, in a manner depending thereon, an auxiliary parameter which is a measure of the intensity of the vapour bubbling that has had an influence on the measured signal in question, and hence a measure of the tissue temperature in the region of that place where the measured signal in question was tapped on the body. For the purpose of ascertaining the auxiliary parameter, the control unit 26 may have recourse to further input parameters, in particular a current value of the air pressure supplied by a pressure sensor 34. A memory 36 connected to the control unit 26 contains information, stored in tabular or algorithmic form, concerning the relationship between the auxiliary parameter and all the input parameters, including the spectral parameters $f_0$, $A_0$ and the air pressure. Depending on the auxiliary parameter ascertained in this way, the control unit 26 then controls the output power of the generator 22 in accordance with a control program. For example, for this purpose a desired-value profile of the auxiliary parameter, suitable for the respective treatment, may have been saved in the memory 36, in response to which the control unit 26 adjusts the auxiliary parameter by power regulation of the generator 22. Alternatively or additionally, one or more thresholds may have been stored in the memory 36, and the control unit 26 may change the power of the generator in stepped manner when said thresholds are fallen short of or exceeded. It will be understood that the concrete control method may depend on the type of the respective treatment.

As an alternative or in addition to the automatic power regulation of the generator 22 outlined above, the thermosurgical apparatus may be open to a manual generator control. For this purpose a display unit 38 on which the control unit 26 can bring about a graphical or numerical display of the ascertained frequency spectrum or at least of the characteristic spectral parameters of the spectrum may have been connected to the control unit 26. It is also conceivable that the control unit 26 can bring about on the display unit 38 the display of a temperature measure derived from the ascertained frequency spectrum and, where appropriate, from further input parameters, which is representative of the estimated tissue temperature. On the basis of the information displayed by the display unit 38, the user can then adapt the power of the generator 22 manually himself via suitable operating elements (not represented in any detail). Such a configuration of the thermosurgical apparatus according to the invention (that is to say, with display of suitable information on the display unit 38 for the purpose of enabling a manual power regulation of the generator instead of an automatic power regulation) is reserved here expressly as possible subject-matter of an application for protection that is yet to be formulated.

The thermosurgical apparatus shown in FIG. 3 may additionally include a source of constant voltage or of constant current (not represented), which provides a stabilised d.c. voltage or a stabilised direct current, respectively. This d.c. voltage or this direct current is fed into the tissue 20. In this way it can be ensured that in the event of a possible subtraction of all electrochemical voltages of the body nevertheless a sufficient voltage swing for the voltage fluctuations caused by vapour bubbles is possible. Expediently this external voltage supply or current supply is such that it has no electrophysiological effects on the biological tissue.

According to another embodiment variant, the thermosurgical apparatus may include an a.c. source (likewise not represented) which provides a constant alternating current, the frequency of which is different from the frequency of the treatment a.c. voltage of the generator 22. This alternating current is fed into the tissue 20. On the body an a.c. voltage can then be tapped, the amplitude of which is modulated in accordance with the changes in tissue impedance caused by bubbles. By envelope demodulation of the a.c. voltage tapped in this way, a measured signal that is representative of the tissue impedance can be obtained which can subsequently be subjected to a spectral analysis in the manner described above.

Generally, the frequency of this additional "measuring alternating current" fed into the tissue for impedance-measuring purposes may be chosen within a wide range, so long as it is sufficiently different from the frequency of the treatment alternating voltage of the generator 22 in order that the voltage response of the body to the excitation by the measuring alternating current can be discriminated from the treatment alternating voltage. Accordingly, the frequency of the measuring alternating current may be chosen, for example, within a range that ranges from approximately 5 kHz up to approximately 10 MHz. By way of typical frequencies of the measuring alternating current, 50 kHz or 100 kHz, for example, may be mentioned. The frequency of the measuring alternating current may be lower or higher than the frequency of the treatment alternating voltage.

By way of a further possible measured quantity which is influenced by the tissue impedance, the phase shift between the measuring alternating current fed in and the tapped alternating-voltage response may be drawn upon. Depending on the value of the tissue impedance, the phase position of the two oscillations relative to one another changes. This can be ascertained by the control unit 26 and likewise evaluated spectrally.

According to a further variant, the tissue impedance could be ascertained directly from the quantities constituted by voltage and current of the HF energy output by the generator 22 (e.g. ratio of the rms values, relative phase position). In this case, a separate measuring alternating current can be dispensed with, this having a favourable effect on the costs of the thermosurgical apparatus.

The invention claimed is:

1. Apparatus for thermal surgery, comprising:
   a generator for providing treatment energy;
   a measuring device for registering a temporal progression of a measured quantity that is influenced by the tissue impedance of a treated body or representative of the tissue impedance; and
   a control unit for determining, based on the measured quantity, a frequency spectrum within a predetermined examination frequency range, the frequency spectrum representative of a temporal progression of the tissue impedance, and for controlling the energy output of the generator based on the determined frequency spectrum, wherein an upper limit of the examination frequency range lies at most at approximately 5 kHz.

2. Apparatus according to claim 1, wherein the upper limit of the examination frequency range lies at least at approximately 80 Hz.

3. Apparatus according to claim 1, wherein the upper limit of the examination frequency range lies at least at approximately 100 Hz.

4. Apparatus according to claim 1, wherein the upper limit of the examination frequency range lies at least at approximately 200 Hz.

5. Apparatus according to claim 1, wherein a lower limit of the examination frequency range lies at most at approximately 2 Hz.

6. Apparatus according to claim 1, wherein a lower limit of the examination frequency range lies at least at approximately 1 Hz.

7. Apparatus according to claim 1, wherein a lower limit of the examination frequency range lies at least at approximately 0.5 Hz.

8. Apparatus according to claim 1, wherein a lower limit of the examination frequency range lies at least at approximately 0.1 Hz.

9. Apparatus according to claim 1, wherein the control unit is adapted to determine one or more characteristic spectral parameters from the frequency spectrum and to control the energy output of the generator based on at least one of the one or more characteristic spectral parameters.

10. Apparatus according to claim 9, wherein the one or more characteristic spectral parameters include a characteristic frequency of the frequency spectrum.

11. Apparatus according to claim 10, wherein the characteristic frequency is a frequency at which the frequency spectrum possesses an amplitude maximum.

12. Apparatus according to claim 10, wherein the control unit is adapted to lower an output power of the generator during a treatment procedure in response to a diminution of the characteristic frequency.

13. Apparatus according claim 9, wherein the one or more characteristic spectral parameters include a characteristic amplitude of the frequency spectrum.

14. Apparatus according to claim 13, wherein the characteristic amplitude is a maximum amplitude of the frequency spectrum.

15. Apparatus according to claim 14, wherein the control unit is adapted to lower an output power of the generator during a treatment procedure in response to an increase of the characteristic amplitude.

16. Apparatus according to claim 15, wherein the control unit is adapted to derive, based on a plurality of input parameters, at least some of which are characteristic of the frequency spectrum, an auxiliary parameter that is representative of a tissue temperature and to control the energy output of the generator based on the auxiliary parameter.

17. Apparatus according to claim 16, wherein for the derivation of the auxiliary parameter the control unit is adapted to access stored information concerning a relationship, ascertained in advance, between the input parameters and a tissue temperature.

18. Apparatus according to claim 16, wherein the control unit is adapted to regulate the energy output of the generator based on at least one target value of the auxiliary parameter.

19. Apparatus according to claim 16, wherein the control unit is adapted to change the energy output of the generator such as in a stepped manner, in response to at least one predetermined threshold of the auxiliary parameter being reached.

20. Apparatus according to claim 16 wherein one of the input parameters is representative of an ambient air pressure.

21. Apparatus according to claim 1 wherein the control unit is adapted to present at least one of the frequency spectrum and at least one quantity derived therefrom on a display unit for visual representation.

* * * * *